United States Patent
Seong

(10) Patent No.: US 10,322,618 B2
(45) Date of Patent: Jun. 18, 2019

(54) ODOR REPRODUCING APPARATUS OF HVAC SYSTEM FOR VEHICLE

(71) Applicant: Hyundai Motor Company, Seoul (KR)

(72) Inventor: Kwang Mo Seong, Whasung-Si (KR)

(73) Assignee: Hyundai Motor Company, Seoul (KR)

( * ) Notice: Subject to any disclaimer, the term of this patent is extended or adjusted under 35 U.S.C. 154(b) by 271 days.

(21) Appl. No.: 15/376,832

(22) Filed: Dec. 13, 2016

(65) Prior Publication Data

US 2017/0368904 A1    Dec. 28, 2017

(30) Foreign Application Priority Data

Jun. 27, 2016    (KR) .................. 10-2016-0080278

(51) Int. Cl.
| | | |
|---|---|---|
| *B60H 1/00* | (2006.01) | |
| *B60H 3/02* | (2006.01) | |
| *B60H 3/06* | (2006.01) | |
| *G01F 1/34* | (2006.01) | |
| *G01N 33/00* | (2006.01) | |
| *G01M 99/00* | (2011.01) | |

(52) U.S. Cl.
CPC ......... *B60H 1/00585* (2013.01); *B60H 1/008* (2013.01); *B60H 3/022* (2013.01); *B60H 3/06* (2013.01); *G01F 1/34* (2013.01); *G01M 99/00* (2013.01); *G01N 33/0001* (2013.01)

(58) Field of Classification Search
CPC .... B60H 1/00585; B60H 3/022; B60H 1/008; B60H 3/06; G01M 99/00; G01N 33/0001; G01F 1/34
See application file for complete search history.

(56) References Cited

U.S. PATENT DOCUMENTS

| | | | | |
|---|---|---|---|---|
| 3,662,818 A | * | 5/1972 | Snyder ................. | B60H 3/0085 165/202 |
| 4,286,141 A | * | 8/1981 | MacCracken ......... | F24H 7/0416 165/10 |
| 4,494,597 A | * | 1/1985 | Fukami .............. | B60H 1/00007 165/41 |
| 4,677,902 A | * | 7/1987 | Takemasa ............ | B60H 3/0007 261/DIG. 65 |

(Continued)

FOREIGN PATENT DOCUMENTS

| | | |
|---|---|---|
| KR | 10-2005-0096579 A | 10/2005 |
| KR | 10-2005-0112275 A | 11/2005 |

(Continued)

*Primary Examiner* — Claire E Rojohn, III
(74) *Attorney, Agent, or Firm* — Morgan, Lewis & Bockius LLP

(57) ABSTRACT

An odor reproducing apparatus of a HVAC system for the vehicle may include an odor reproducing device configured to reproduce and evaluate odor by applying a HVAC system module, a heat exchange outdoor device mounted at one side of the odor reproducing device to control a temperature and humidity of an experimental space, and a control device mounted at one side of the odor reproducing device and the heat exchange outdoor device to control an operation of the odor reproducing device and an operation of the heat exchange outdoor device to implement a field environment and vehicle conditions for evaluating an odor improvement effect of the HVAC system reflecting an odor reduction technology.

7 Claims, 6 Drawing Sheets

(56) References Cited

U.S. PATENT DOCUMENTS

| | | | | |
|---|---|---|---|---|
| 5,320,577 | A * | 6/1994 | Tooru | B60H 1/008 454/139 |
| 7,913,540 | B2 * | 3/2011 | Brasfield | G01N 33/0057 73/23.34 |
| 8,219,249 | B2 * | 7/2012 | Harrod | G05B 19/042 700/276 |
| 2004/0007000 | A1 * | 1/2004 | Takeda | A61L 9/22 62/78 |
| 2005/0279110 | A1 * | 12/2005 | Zeng | B60H 1/0075 62/176.6 |
| 2010/0330895 | A1 * | 12/2010 | Suetake | B60H 1/00785 454/75 |
| 2012/0015594 | A1 * | 1/2012 | Yenneti | B60H 1/00742 454/75 |
| 2013/0055746 | A1 * | 3/2013 | Yokoo | F25B 41/04 62/238.1 |
| 2014/0262132 | A1 * | 9/2014 | Connell | B60H 1/00457 165/11.1 |
| 2015/0122472 | A1 * | 5/2015 | Higuchi | B60H 1/00849 165/202 |

FOREIGN PATENT DOCUMENTS

| | | |
|---|---|---|
| KR | 10-2007-0045721 A | 5/2007 |
| KR | 10-2011-0043887 A | 4/2011 |
| KR | 10-2015-0114694 A | 10/2015 |
| KR | 10-2016-0070983 A | 6/2016 |

\* cited by examiner

ODOR REPRODUCING APPARATUS OF HVAC SYSTEM FOR VEHICLE

CROSS-REFERENCE TO RELATED APPLICATION

The present application claims priority to Korean Patent Application No. 10-2016-0080278 filed on Jun. 27, 2016, the entire contents of which is incorporated herein for all purposes by this reference.

BACKGROUND OF THE INVENTION

Field of the Invention

The present invention relates to an odor reproducing apparatus for evaluating an odor improvement effect of a heating, ventilating, and air-conditioning (HVAC) system for a vehicle.

Description of Related Art

As the quality of life is improved together with the economic growth, there is growing interest of a consumer in health and wellbeing. Accordingly, limitation on the quality of internal air in a multi-use facility or a vehicle has been increased.

A vehicle manufacturer manages seven types of volatile organic compounds (VOCs) such as toluene in order to deal with the limitation on the quality of internal air in a new vehicle. Further, in order to reduce dissatisfaction with odor of the consumer, the VOCs are increasingly managed by increasing application of an odor reduction material.

In recent years, dissatisfaction of a consumer with respect to air vent odor of used vehicles has increased together with VOCs/odor of a new vehicle.

That is, unpleasant odor of air vent in the used vehicle occurs due to following three factors.

First, when a HVAC system is operated in an external air mode, odor materials in atmosphere such as smoke or excretion odor are introduced and generated. Second, the odor materials introduced into the HVAC system from external air/indoor are absorbed in HVAC components such as a filter and are desorbed to be generated. Third, odor-causing microbe floating in atmosphere is introduced into the HVAC system to be adhered to HVAC components such as an evaporator so that a bio film is formed and microbe (m) HVACs being metabolic by-product created through a metabolism are exhausted and generated.

Accordingly, a vehicle manufacturer and HVAC partners enlarge development and application of a combination filter containing activated carbon, an ionizer with sterilization and deodorization functions in order to reduce unpleasant odor of an air vent, and antibiotic coating evaporator in order to suppress growth of microbes.

However, although the above improvement is tried, there is growing dissatisfaction of a consumer with the pleasant odor of the air vent. The reason of increasing the dissatisfaction of a consumer with the pleasant odor of the air vent including a case of deteriorating a vehicle dependability study (VDS) and a quality index with respect to the pleasant odor of the air vent is determined as one reason not to suitably achieve odor improvement effect evaluation together with a product performance evaluation of an odor reduction technology.

Accordingly, there is a need to develop an odor reproducing device reflecting a use condition of the consumer in order to evaluate an improvement effect with respect to the odor reduction technology.

The information disclosed in this Background of the Invention section is only for enhancement of understanding of the general background of the invention and should not be taken as an acknowledgement or any form of suggestion that this information forms the prior art already known to a person skilled in the art.

BRIEF SUMMARY

Various aspects of the present invention are directed to providing an odor reproducing apparatus of a HVAC system for a vehicle having advantages of implementing a field environment and a vehicle condition to be implemented to evaluate an odor improvement effect of a HVAC system reflecting an odor reduction technology.

Various aspects of the present invention are directed to providing an odor reproducing apparatus of a HVAC system for the vehicle may include an odor reproducing device configured to reproduce and evaluate odor by applying a HVAC system module, a heat exchange outdoor device mounted at one side of the odor reproducing device to control a temperature and humidity of an experimental space, and a control device mounted at one side of the odor reproducing device and the heat exchange outdoor device to control an operation of the odor reproducing device and an operation of the heat exchange outdoor device.

The odor reproducing device may include a temperature/humidity control chamber configured to control a temperature and humidity of introduced air; an external air simulation chamber configured to receive dust, malodorous microbes, and pollution gas; an internal air simulation chamber configured to reproduce HVAC odor by applying a HVAC system module; and an odor evaluating device configured to evaluate the reproduced HVAC odor.

The temperature/humidity control chamber may include an external air inlet configured to introduce external air, a pre-filter configured to remove dust from the introduced external air; an air fan configured to circulate the introduced external air, a heater core configured to heat the circulated air; an evaporator core configured to cool the circulated air, and a humidifier configured to control humidity of the circulated air.

The external air simulation chamber may include an air inlet configured to introduce air having controlled temperature/humidity; a flap door of a rubber material configured to block movement of air from the external air simulation chamber to the temperature/humidity control chamber while allowing the movement of air from the temperature/humidity control chamber to the external air simulation chamber; and a pollution material supply portion configured to inject a pollution material in the pollution material supply portion.

The internal air simulation chamber may include a pollution air inlet configured to introduce air having controlled temperature/humidity mixed with a pollution material into the temperature/humidity control chamber, an outdoor device configured to supply or recover coolant to or from the evaporator core, and a hot water supply portion configured to supply and recover hot water to and from the heater core.

The odor evaluating device may include a first damper configured to reproduce an external air mode; a second damper configured to reproduce an internal air mode; and an odor evaluating vent connected with a sensuality evaluation line to evaluate sensuality.

The control device may include a main switch configured to supply power to an entire device; and a controller configured to control operations of the odor reproducing device and a heat exchange outdoor device.

The control device may include a voltmeter configured to indicate a voltage of power applied to the whole evaluating device; an ammeter configured to indicate a current, a differential pressure gauge configured to confirm a flow rate of air exhausted from the internal air simulation chamber; a timer configured to indicate an operation time of equipment; and a temperature/humidity monitoring device configured to store measurement data while indicating temperature and humidity changes of each space as a graph.

The controller may include a monitoring screen configured to indicate an operation state of entire equipment; and a pattern setting screen configured to set an operation condition.

According to an exemplary embodiment of the present invention, since odor reproduction reflecting a field condition is possible, an odor influence due to absorption/desorption of indoor/outdoor introduction odor materials in a HVAC system may be evaluated. An odor influence due to multiplication of microbe and generation of a by-product in a surface of an evaporator may be evaluated. An odor influence due to seasonal (temperature/humidity change and environmental (air pollution, dust, etc.) factors may be evaluated. An odor influence due to user characteristic (air conditioner use pattern, air volume, etc.) factor may be evaluated.

Further, new technology screening and optimal technology combination may be obtained by reinforcing an improvement effect verification of an odor reduction technology so that an affective quality including odor can be improved.

The methods and apparatuses of the present invention have other features and advantages which will be apparent from or are set forth in more detail in the accompanying drawings, which are incorporated herein, and the following Detailed Description, which together serve to explain certain principles of the present invention.

Figure 1:
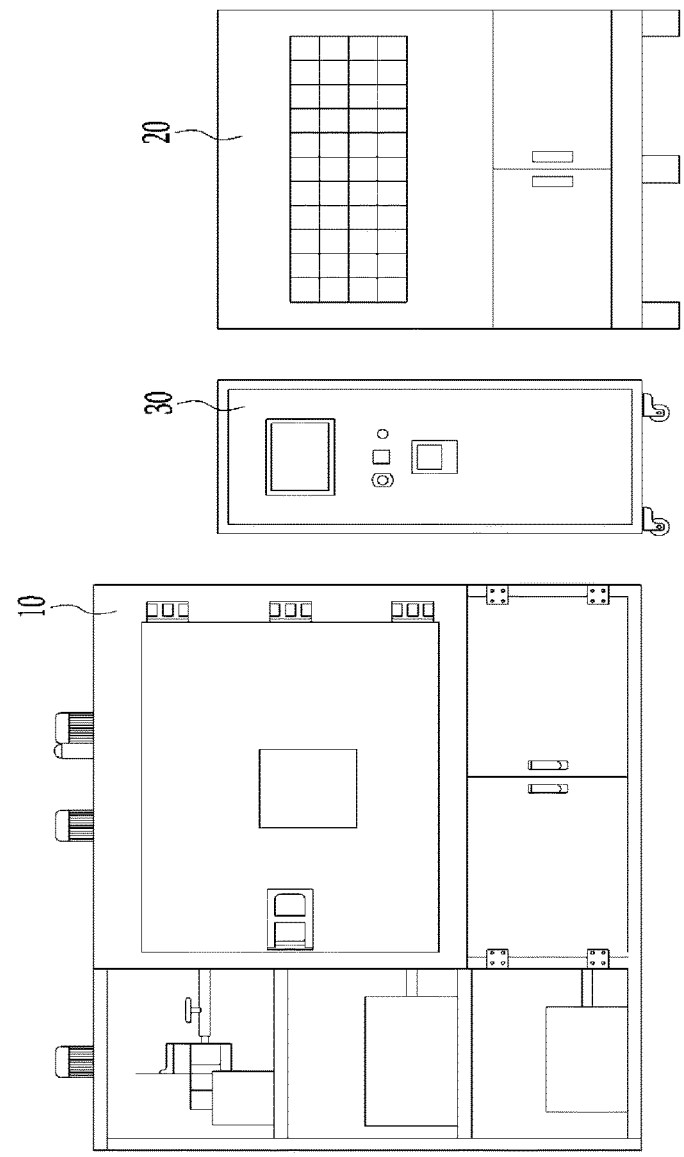
FIG. 1 is a view schematically illustrating an odor reproducing apparatus of a HVAC system according to an exemplary embodiment of the present invention.

It should be understood that the appended drawings are not necessarily to scale, presenting a somewhat simplified representation of various features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

Reference will now be made in detail to various embodiments of the present invention(s), examples of which are illustrated in the accompanying drawings and described below. While the invention(s) will be described in conjunction with exemplary embodiments, it will be understood that the present description is not intended to limit the invention(s) to those exemplary embodiments. On the contrary, the invention(s) is/are intended to cover not only the exemplary embodiments, but also various alternatives, modifications, equivalents and other embodiments, which may be included within the spirit and scope of the invention as defined by the appended claims.

Hereinafter, an example embodiment of the present invention will be described in detail with reference to the accompanying drawings.

The terms used in the specification are for explaining specific exemplary embodiments and have no intention to limit the present invention. Unless the context indicates otherwise, the singular expression may include the plural expression. In the following description, the term "include" or "has" will be used to refer to the feature, the number, the step, the operation, the component, the part or the combination thereof without excluding the presence or addition of one or more features, the numbers, the steps, the operations, the components, the parts or the combinations thereof.

In the following detailed description, only certain exemplary embodiments of the present invention have been shown and described, simply by way of illustration. It should be understood that numerous other modifications and following exemplary embodiments can be devised by those skilled in the art that will fall within the spirit and scope of the principles of the present invention. As those skilled in the art would realize, the described embodiments may be modified in various different ways, all without departing from the spirit or scope of the present invention.

FIG. 1 is a view schematically illustrating an odor reproducing apparatus of a HVAC system according to an exemplary embodiment of the present invention.

As shown in FIG. 1, included is an odor reproducing apparatus capable of reproducing HVAC odor where a HVAC implements general atmospheric environment conditions (temperature, humidity, dust, microbes, pollution gas, etc.) to which a HVAC system is exposed, vehicle conditions (cooling of evaporator core due to coolant, and heating of a heater core due to hot water), and user conditions (air conditioner use pattern, etc.) when the vehicle is operated and stops.

The odor reproducing apparatus is configured to take into consideration interaction between HVAC components or odor reduction technology and to evaluate odor contributions by components by applying a HVAC system module to odor reproducing evaluation.

The odor reproducing apparatus of a HVAC system for the vehicle according to an exemplary embodiment of the present invention includes: an odor reproducing device 10 configured to reproduce and evaluate odor by applying a HVAC system module, a heat exchange outdoor device 20 mounted at one side of the odor reproducing device 10 to control a temperature and humidity of an experimental space, and a control device 30 mounted at one side of the odor reproducing device 10 and the heat exchange outdoor device 20 to control an operation of the odor reproducing device 10 and an operation of the heat exchange outdoor device 20.

Figure 2:
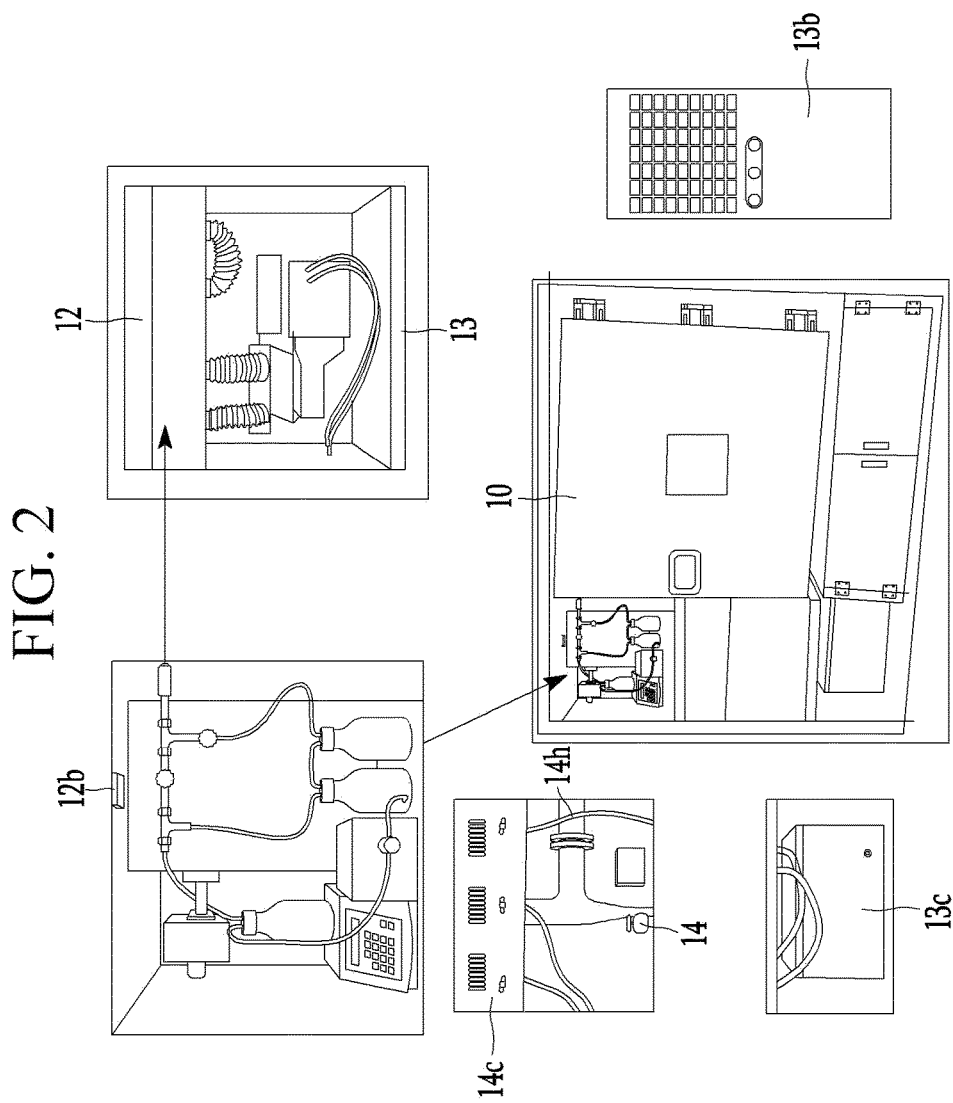
FIG. 2 is a view schematically illustrating a configuration of an odor reproducing device according to an exemplary embodiment of the present invention.

FIG. 2 is a view schematically illustrating a configuration of an odor reproducing device according to an exemplary embodiment of the present invention.

Figure 3:
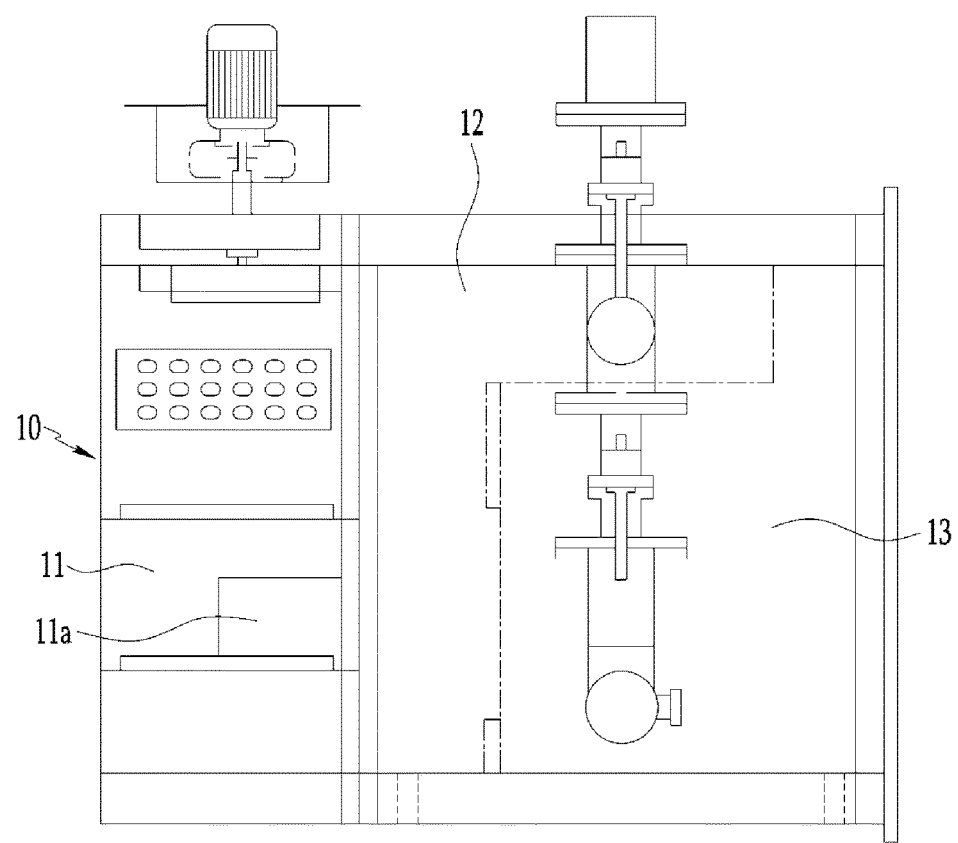
FIG. 3 is a view schematically illustrating an internal structure of an odor reproducing device according to an exemplary embodiment of the present invention.

FIG. 3 is a view schematically illustrating an internal structure of an odor reproducing device according to an exemplary embodiment of the present invention.

Figure 4:
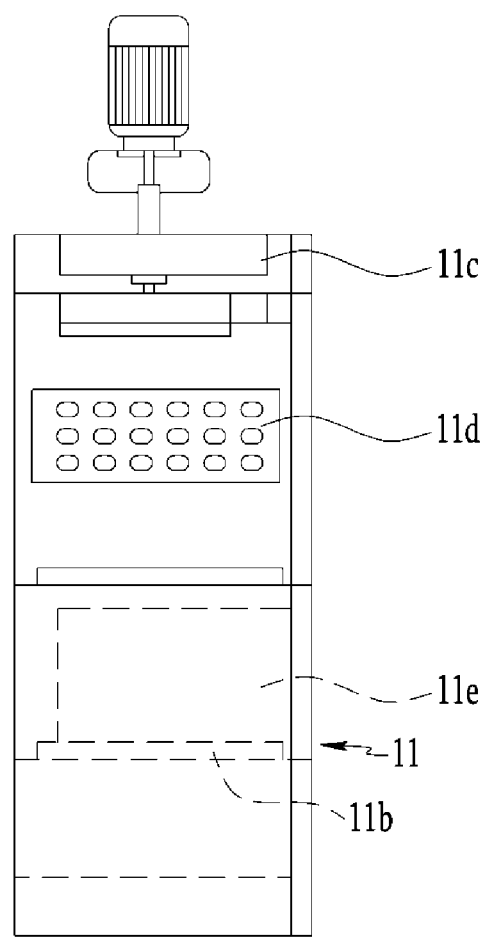
FIG. 4 is a view schematically illustrating a structure of a temperature/humidity control chamber according to an exemplary embodiment of the present invention.

FIG. 4 is a view schematically illustrating a structure of a temperature/humidity control chamber according to an exemplary embodiment of the present invention.

Figure 5:
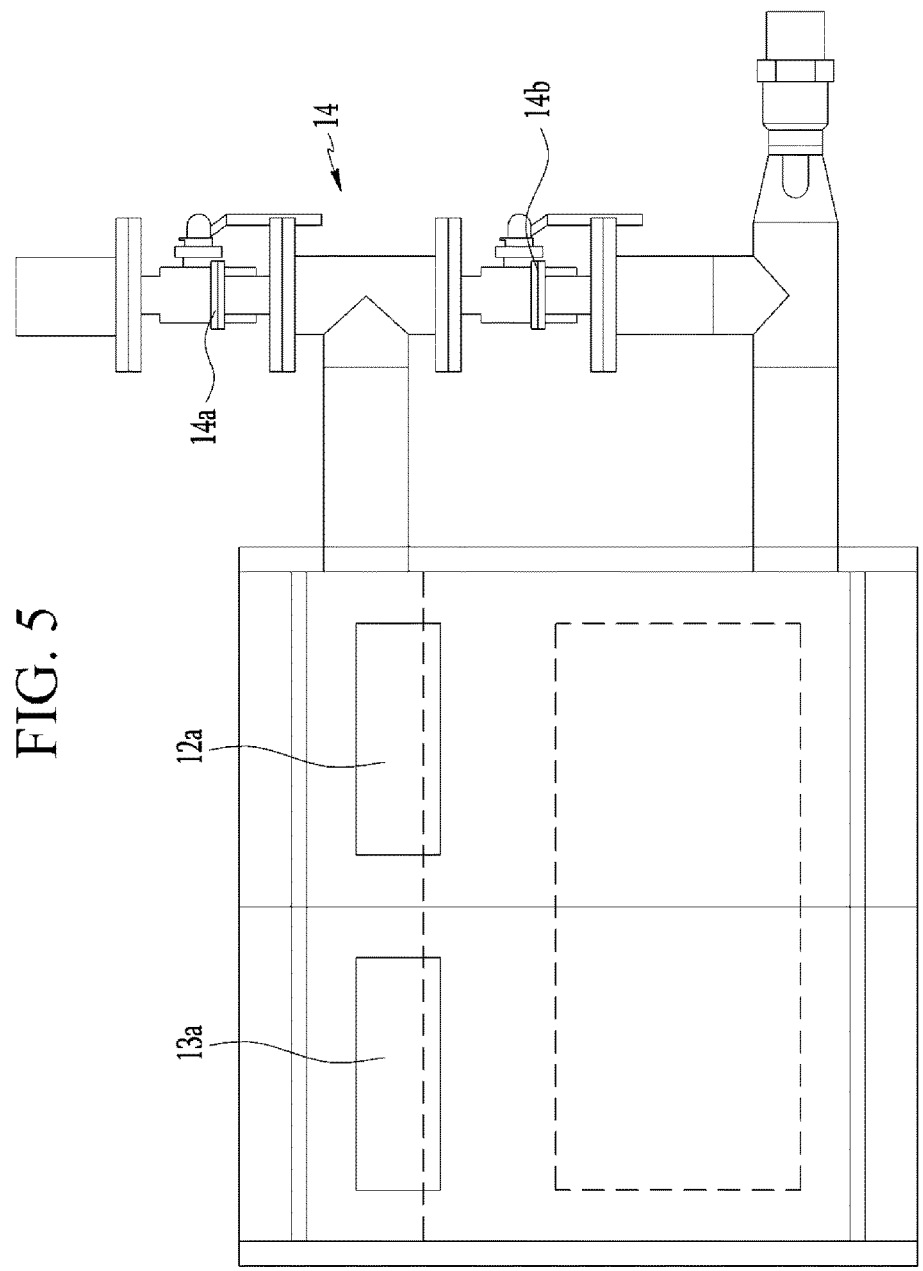
FIG. 5 is a view schematically illustrating a structure of an odor evaluating device according to an exemplary embodiment of the present invention.

FIG. 5 is a view schematically illustrating a structure of an odor evaluating device according to an exemplary embodiment of the present invention.

As shown in FIG. 2 to FIG. 5, the odor reproducing device 10 includes a temperature/humidity control chamber 11 configured to control a temperature and humidity of introduced air, an external air simulation chamber 12 configured to receive dust, malodorous microbes, and pollution gas, an internal air simulation chamber 13 configured to reproduce HVAC odor by applying a HVAC system module, and an odor evaluating device 14 configured to evaluate the reproduced HVAC odor.

Further, the temperature/humidity control chamber 11 may include an external air inlet 11*a* configured to introduce external air, a pre-filter 11*b* configured to remove dust from the introduced external air, an air fan 11*c* configured to circulate the introduced external air, a heater core 11*d* configured to heat the circulated air, an evaporator core 11*e* configured to cool the circulated air, and a humidifier configured to control humidity of the circulated air.

In the instant case, the external air simulation chamber 12 connected with the temperature/humidity control chamber 11 may include an air inlet 12*a* configured to introduce air having controlled temperature/humidity, a flap door of a rubber material configured to block movement of air from the external air simulation chamber 12 to the temperature/humidity control chamber 11 while allowing the movement of air from the temperature/humidity control chamber 11 to the external air simulation chamber 12, and a pollution material supply portion 12*b* configured to inject a pollution material therein.

Moreover, the pollution material supply portion 12*b* may include an air pump, a dust supply device configured to supply dust, a peristaltic pump configured to supply malodorous microbes, an ultrasonic wave generator, an ultrasonic wave spray nozzle, and a gas supply device configured to supply pollution gas.

Further, the internal air simulation chamber 13 may include a pollution air inlet 13*a* configured to introduce air having controlled temperature/humidity mixed with a pollution material into the temperature/humidity control chamber 11, an outdoor device 13*b* configured to supply or recover coolant to or from the evaporator core 11*e*, and a hot water supply portion 13*c* configured to supply and recover hot water to and from the heater core 11*d*.

The outdoor device 13*b* may include a first coolant supply device configured to control a temperature of the temperature/humidity control chamber 11, and a second coolant supply device configured to control a temperature of the internal air simulation chamber 13.

The first coolant supply device may include an R-12 first coolant supply compressor, a first coolant supply pipe, a first pressure sensor configured to check pressure coolant to be supplied, and a first coolant recovery pipe.

The second coolant supply device may include an R-134a second coolant supply compressor, a second coolant supply pipe, a second pressure sensor, and a second coolant recovery pipe used to cool an evaporator core 11*e* of the HVAC system, a coolant recovery nozzle configured to reduce consumption of coolant during replacement of the HVAC system, a supply pipe cut-off valve configured to cut-off flow of the coolant, and a recovery pipe cut-off valve.

In addition, the internal air simulation chamber 13 may further include a coolant supply pipe configured to supply coolant to the evaporator core 11*e* of the HVAC system, a coolant recovery pipe configured to recover the coolant from the evaporator core 11*e* of the HVAC system, a hot water supply pipe and a hot water recovery pipe configured to supply/recover hot water to and from the heater core 11*d*, a power supply device configured to supply power to a blower motor to operate a blower of the HVAC system, a wiring and a connector, and an air outlet configured to exhaust reproduced odor.

Meanwhile, the odor evaluating device 14 of the odor reproducing apparatus may include a first damper 14*a* configured to reproduce an external air mode, a second damper 14*b* configured to reproduce an internal air mode, and an odor evaluating vent 14*c* connected with a sensuality evaluation line 14*h* to evaluate sensuality.

The odor evaluating device 14 may include a divider having a sensuality evaluation line 14*h* and a precision analysis line, and an opening and shutting valve configured to leak/block air containing odor.

Figure 6:
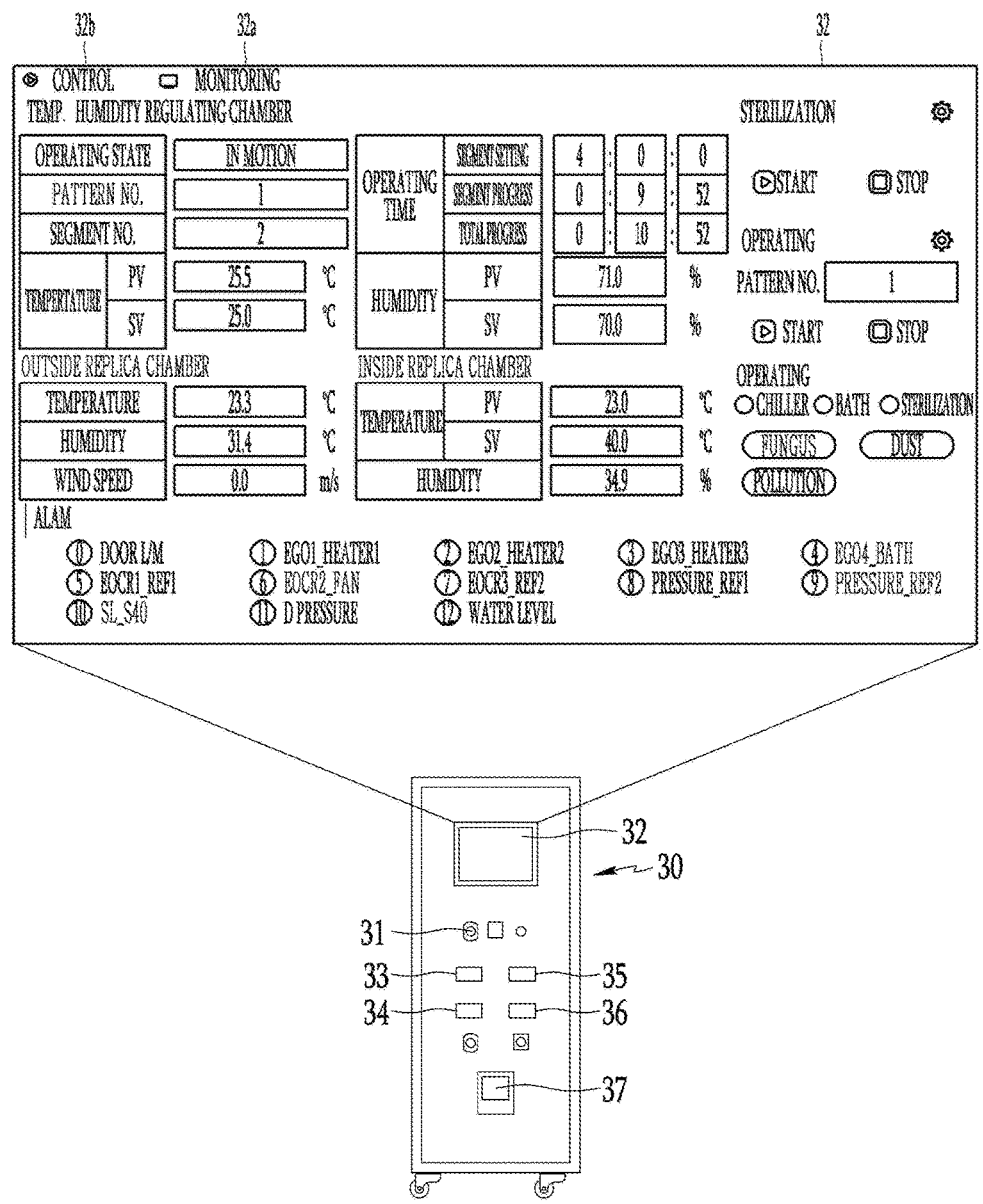
FIG. 6 is a view schematically illustrating a configuration of a control device according to an exemplary embodiment of the present invention.

FIG. 6 is a view schematically illustrating a configuration of a control device according to an exemplary embodiment of the present invention.

As shown in FIG. 6, the control device 30 may include a main switch 31 configured to supply power to an entire device, and a controller 32 configured to control an operation of the odor reproducing device and a heat exchange outdoor device.

Moreover, the control device 30 may include a voltmeter 33 configured to indicate a voltage of power applied to the whole evaluating device, an ammeter 34 configured to indicate a current, a differential pressure gauge 35 configured to confirm a flow rate of air exhausted from the internal air simulation chamber 13, a timer 36 configured to indicate an operation time of equipment, and a temperature/humidity monitoring device 37 configured to store measurement data while indicating temperature and humidity changes of each space as a graph.

The controller 32 may include a monitoring screen 32*a* configured to indicate an operation state of entire equipment, and a pattern setting screen 32*b* configured to set an operation condition.

Further, the monitoring screen 32*a* of the controller 32 may include a temperature/humidity control chamber display window configured to indicate an operation state (operation/end), a pattern number to which conditions including temperature/humidity/retention time/pollution material supply time is set, and temperature/humidity (predetermined value/measurement value), and an operation time of the temperature/humidity control chamber 11; an external air simulation chamber display window configured to indicate a temperature, humidity and wind speed/wind volume of the external air simulation chamber 12; an internal air simulation chamber display window configured to indicate temperature (predetermined value/measurement value) and/humidity of the internal air simulation chamber 13; a sterilization display window configured to perform heat treatment at 220° C. to sterilize microbes absorbed in the odor evaluating device 14 and to desorb VOCs; an operation display window configured to control pattern number determination and start/operation; and a state display window configured to indicate pollution material/coolant/hot water supply state; and an alarm display window configured to display problems of the entire device.

The pattern setting screen 32b allows a user to input a pattern number, temperature/humidity/time, opening/shutting time signal setting of the first damper 14a and the second damper 14b, pollution material supply, operation setting and the repetition number of times.

According to an exemplary embodiment of the present invention, when the odor reproducing apparatus of a HVAC system for the vehicle performs an experiment, an evaluation preparation step (sterilization/deodorization), an odor reproducing step, and an odor evaluating step are performed.

The evaluation preparation step is as follows.

Recover coolant/hot water to be supplied to a HVAC system in the internal air simulation chamber 13→disassemble a coolant/hot water pipe→separate the HVAC system.

Operate in the order of control device 30→controller 32→monitoring screen 32a→sterilize display window→start button click→sterilization function.

Microbes in all spaces are sterilized and absorbed odor and gaseous materials are desorbed/exhausted by increasing internal temperatures of the temperature/humidity control chamber 11, the external air simulation chamber 12, and the internal air simulation chamber 13 to 220° C. by recovering coolant of the evaporator core 11e in the temperature/humidity control chamber 11, heating the heater core 11d, and operating the air fan 11c, so that an influence factor with respect to an odor reproducing evaluation is remove.

The odor reproducing step is as follows.

Install a HVAC system in the internal air simulation chamber 13→connect coolant/hot water pipe→supply coolant/hot water.

Control device 30→controller 32→pattern setting screen 32b→input pattern number, and temperature/humidity/operation time by segments, and set opening/shutting time signal of a first damper 14a and a second damper 14b, supply pollution materials and configure devices associated with an operation of the HVAC system, and input the repetition number of times→store.

Control device 30→controller 32→monitoring screen 32a→internal air simulation chamber display window→input a test temperature in predetermined value items→operation display window→input a pattern number, and click a start button→operate a reproducing apparatus→reproduce HVAC odor.

The odor evaluating step is as follows.

Control device 30→controller 32→pattern setting screen 32b→input pattern number, and temperature/humidity/operation time by segments, and set opening/shutting time signal of a first damper 14a and a second damper 14b, supply pollution materials and configure devices associated with an operation of the HVAC system, and input the repetition number of times→store.

Control device 30→controller 32→monitoring screen 32a→internal air simulation chamber display window→input a test temperature in predetermined value items→operation display window→input a pattern number, and click a start button→operate a reproducing apparatus→reproduce HVAC odor.

Odor evaluating device 14→open an opening/shutting valve→evaluate sensuality using the odor evaluating vent 14c and collect precision analysis air using a precision analysis line (using a tedlar or an adsorption pipe)→configure sensuality evaluation result check sheet.

Accordingly, since odor reproduction reflecting a field condition is possible, an odor influence due to absorption/desorption of indoor/outdoor introduction odor materials in a HVAC system may be evaluated. An odor influence due to multiplication of microbe and generation of a by-product in a surface of an evaporator may be evaluated. An odor influence due to seasonal (temperature/humidity change and environmental (air pollution, dust, etc.) factors may be evaluated. An odor influence due to user characteristic (air conditioner use pattern, air volume, etc.) factor may be evaluated.

Further, since the HVAC system may be fully evaluated and odor reduction contribution by components/technologies may be evaluated, a totally comparison evaluation is possible in a device of a HVAC system module. Odor influences may be evaluated by components (filter, ionizer, evaporator, heater core, and other components). Odor influences may be evaluated according to whether to apply a new odor reduction technology.

That is, new excellent technology screening and optimal technology combination may be obtained by reinforcing an improvement effect verification of an odor reduction technology so that an affective quality including odor can be improved.

As described above, although exemplary embodiments of the present invention are shown and illustrated, numerous variations and other exemplary embodiments may be performed by those skilled in the art. Numerous other modifications and embodiments are included in the appended claims to be devised by those skilled in the art that will fall within the spirit and scope of the principles of this disclosure For convenience in explanation and accurate definition in the appended claims, the terms "upper", "lower", "inner", "outer", "up", "down", "upper", "lower", "upwards", "downwards", "front", "rear", "back", "inside", "outside", "inwardly", "outwardly", "interior", "exterior", "inner", "outer", "forwards", and "backwards" are used to describe features of the exemplary embodiments with reference to the positions of such features as displayed in the figures.

The foregoing descriptions of specific exemplary embodiments of the present invention have been presented for purposes of illustration and description. They are not intended to be exhaustive or to limit the invention to the precise forms disclosed, and obviously many modifications and variations are possible in light of the above teachings. The exemplary embodiments were chosen and described in order to explain certain principles of the invention and their practical application, to thereby enable others skilled in the art to make and utilize various exemplary embodiments of the present invention, as well as various alternatives and modifications thereof. It is intended that the scope of the invention be defined by the Claims appended hereto and their equivalents.

What is claimed is:

1. An odor reproducing apparatus of a heating, ventilating, and air-conditioning (HVAC) system for a vehicle, the apparatus comprising:
   an odor reproducing device configured to reproduce and evaluate odor by applying a HVAC system module;
   a heat exchange outdoor device mounted at a first side of the odor reproducing device to control a temperature and humidity of an experimental space; and a control device mounted at a second side of the odor reproducing device and the heat exchange outdoor device to control an operation of the odor reproducing device and an operation of the heat exchange outdoor device, wherein the odor reproducing device includes:
a temperature/humidity control chamber controlling a temperature and humidity of an introduced air;
an external air simulation chamber receiving dust, malodorous microbes, and pollution gas;
an internal air simulation chamber reproducing HVAC odor by applying the HVAC system module; and
an odor evaluating device evaluating the reproduced HVAC odor, and wherein the odor evaluating device includes:
a first damper reproducing an external air mode;
a second damper reproducing an internal air mode; and
an odor evaluating vent connected with a sensuality evaluation line to evaluate sensuality.

2. The odor reproducing apparatus of the HVAC system for the vehicle of claim 1, wherein the temperature/humidity control chamber includes:
an external air inlet introducing external air;
a pre-filter removing dust from the introduced external air;
an air fan circulating the introduced external air;
a heater core portion heating the circulated air;
an evaporator core portion cooling the circulated air; and
a humidifier controlling humidity of the circulated air.

3. The odor reproducing apparatus of the HVAC system for the vehicle of claim 1, wherein the external air simulation chamber includes:
an air inlet introducing air having controlled temperature/humidity;
a flap door of a rubber material blocking movement of air from the external air simulation chamber to the temperature/humidity control chamber while allowing a movement of air from the temperature/humidity control chamber to the external air simulation chamber; and a pollution material supply portion injecting a pollution material in the pollution material supply portion.

4. The odor reproducing apparatus of the HVAC system for the vehicle of claim 2, wherein the internal air simulation chamber includes:
a pollution air inlet introducing air having controlled temperature/humidity mixed with a pollution material into the temperature/humidity control chamber;
an outdoor device supplying or recovering coolant to or from the evaporator core portion; and
a hot water supply portion supplying and recovering hot water to and from the heater core portion.

5. The odor reproducing apparatus of the HVAC system for the vehicle of claim 1, wherein the control device includes:
a switch selectively turning on to supply power to an entire device; and
a controller configured to control operations of the odor reproducing device and a heat exchange outdoor device.

6. The odor reproducing apparatus of the HVAC system for the vehicle of claim 5, wherein the control device includes:
a voltmeter indicating a voltage of power applied to an evaluating device;
an ammeter indicating a current;
a differential pressure gauge confirming a flow rate of air exhausted from the internal air simulation chamber;
a timer indicating an operation time of equipment; and
a temperature/humidity monitoring device storing measurement data while indicating temperature and humidity changes of each space as a graph.

7. The odor reproducing apparatus of the HVAC system for the vehicle of claim 5, wherein the controller includes:
a monitoring screen indicating an operation state of entire equipment; and
a pattern setting screen setting an operation condition.

* * * * *